United States Patent [19]

Crotty et al.

[11] Patent Number: 5,766,575
[45] Date of Patent: Jun. 16, 1998

[54] METHOD AND COMPOSITION FOR SKIN LIGHTENING

[75] Inventors: Brian Andrew Crotty, Branford; Alexander Paul Znaiden, Trumbull; Anthony Johnson, Fairfield, all of Conn.

[73] Assignee: Chesebrough-Pond's USA Co., Division of Conopco, Inc., Greenwich, Conn.

[21] Appl. No.: 663,829

[22] Filed: Jun. 14, 1996

[51] Int. Cl.⁶ ........................................ A61K 7/42
[52] U.S. Cl. ................. 424/59; 424/47; 424/60; 424/62
[58] Field of Search ................. 424/47, 59, 60, 424/62

[56] References Cited

U.S. PATENT DOCUMENTS 4,096,240  6/1978  Mathur ........................... 424/59

FOREIGN PATENT DOCUMENTS

| | | |
|---|---|---|
| 0 570 230 | 11/1993 | European Pat. Off. |
| 52-044 375 | 11/1977 | Japan. |
| 61-027 910 | 2/1986 | Japan. |
| 06 048 929 | 2/1994 | Japan. |
| 1 319 455 | 6/1973 | United Kingdom. |
| 2 287 405 | 3/1995 | United Kingdom. |

*Primary Examiner*—Terressa Mosley
*Attorney, Agent, or Firm*—Milton L. Honig

[57] ABSTRACT

A method and composition is provided for treating skin to achieve lightening by employing an active of the structure:

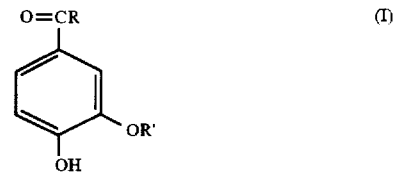

wherein R is selected from the group consisting of hydrogen, hydroxy and $C_1$–$C_{30}$ alkyl or aryl groups radicals; and $R^1$ is selected from the group consisting of hydrogen and $C_1$–$C_{30}$ alkyl or aryl radicals.

12 Claims, No Drawings

METHOD AND COMPOSITION FOR SKIN LIGHTENING

BACKGROUND OF THE INVENTION

1. Field of the Invention

The invention concerns a method and compositions for lightening the color of skin.

2. The Related Art

Ever since the first freckle or hyperpigmented spot appeared on the human face, there has been demand for treatment. Historically treatments have Bleaching of skin with ammoniated mercury and other salts of this metal are reported to be quite effective. Of course there are significant safety issues involved with mercurials.

Zinc peroxide has been utilized in anhydrous ointments as a bleaching agent. Monobenzyl ether of hydroquinone was marketed for its skin lightening effect but questions of safety were here also raised.

Ascorbic acid preparations, either pure or made from some natural material, such as lemon juice, were suggested as useful. While seemingly entirely safe, they do not seem to be very effective.

U.S. Pat. No. 4,096,240 (Mathur) refers to niacin as effective in skin lightening. This material is postulated to operate by retarding melanin dispersion or distribution into the epidermis. Since unpleasant skin flushing occurs with niacin, the patent suggests use of niacinamide as a substitute. Compositions based upon niacinamide are effective, but only to a limited extent.

Accordingly, it is an object of the present invention to provide a skin lightening composition and actives to accomplish this function which are more efficient than materials heretofore known and are safe to use.

Another object of the present invention is to provide a skin lightening composition and actives to accomplish this function which are particularly effective against agespots, freckles and hyperpigmentation.

These and other objects of the present invention will become more readily apparent from consideration of the following summary and detailed description.

SUMMARY OF THE INVENTION

A method for lightening the color of skin is provided which includes applying to the skin a compound of the structure (1):

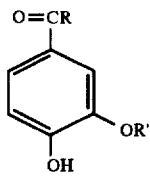

wherein R is selected from the group consisting of hydrogen, hydroxy and $C_1$–$C_{30}$ alkyl or aryl groups radicals; and $R^1$ is selected from the group consisting of hydrogen and $C_1$–$C_{30}$ alkyl or aryl radicals.

A composition for skin lightening is also provided which includes:

(i) an effective amount to achieve skin lightening of an active having structure (I);
(ii) from 0.1 to 30% by weight of a sunscreen agent; and
(iii) a pharmaceutically acceptable carrier to deliver structure (I) and the sunscreen agent.

DETAILED DESCRIPTION OF THE INVENTION

Now it has been discovered that vanillin, vanillic acid and its derivatives are active agents in lightening skin. These actives are effective against hyperpigmentation, agespots and freckles. They have the general structure (I):

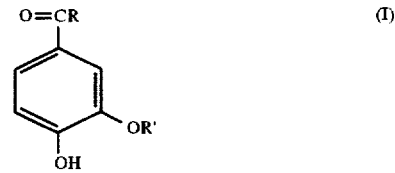

wherein R is selected from the group consisting of hydrogen, hydroxy and $C_1$–$C_{30}$ alkyl or aryl groups radicals; and $R^1$ is selected from the group consisting of hydrogen and $C_1$–$C_{30}$ alkyl or aryl radicals.

Amounts of the active (I) may range from 0.1 to 20%, preferably from 0.5 to 10%, optimally from 1 to 5% by weight.

Use of (I) may be according to a regime that applies compositions containing the active repeatedly to the same area of the skin. For instance, application can be done daily for periods from several days to several weeks, before skin lightening becomes evident.

In a further aspect of the invention, the action of the skin lightening active (I) is ensured against reversal of melanisation through the presence of an ultraviolet absorbing sunscreen. By the term "sunscreen" is meant any material whether organic or inorganic which can shield the skin from ultraviolet radiation within the range of 290 to 400 nm.

When the sunscreen is an organic material, it will usually contain at least one chromophoric agent absorbing within the ultraviolet range somewhere from 290 to 400 nm. Chromophoric organic sunscreen agents may be divided into the following categories (with specific examples) including: p-Aminobenzoic acid, its salts and its derivatives (ethyl, isobutyl, glyceryl esters; p-dimethylaminobenzoic acid); Anthranilates (o-aminobenzoates; methyl, methyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); Cinnamic acid derivatives (menthyl and benzyl esters, α-phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naptholsulfonates (sodium salts of 2-naphthol-3,6-disulfonic and of 2-naphthol-6,8-disulfonic acids); Dihydroxy-napthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride oleate and tannate); Quinoline derivatves (8-hydroxyquinoline salts, 2-phenylquinoline); Hydroxy-or methoxy-substituted benzophenones; Uric and vilouric acids; Tannic acid and its derivatives (e.g. hexaethylether); (Butyl carbityl) (6-propyl piperonyl) ether; Hydroquinone; Benzophenones (Oxybenzone, Sulisobenzone, Dioxybenzone, Benzoresorcinol, 2,2',4,4'-Tetrahydroxybenzophenone, 2,2'-Dihydroxy-4,4'-dimethoxybenzophenone, Octabenzone;

4-isopropyldibenzoylmethane, Butylmethoxydibenzoylmethane; Etocrylene; and 4-isopropyl-dibenzoylmethane).

Particularly useful are: 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl-4-[(bis(hydroxypropyl)] aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl)-5-sulfoniobenzoxazoic acid and mixtures thereof.

Suitable commercially available organic sunscreen agents are those identified under the following table.

TABLE I

| CTFA NAME | TRADE NAME | SUPPLIER |
|---|---|---|
| Benzophenone-3 | UVINUL M-40 | BASF Chemical Co. |
| Benzophenone-4 | UVINUL MS-40 | BASF Chemical Co. |
| Benzophenone-8 | SPECTRA-SORB UV-24 | American Cyanamid |
| DEA-Methoxycinnamate | BERNEL HYDRO | Bernel Chemical |
| Ethyl dihydroxypropyl-PABA | AMERSCREEN P | Amerchol Corp. |
| Glyceryl PABA | NIPA G. M. P. A. | Nipa Labs. |
| Homosalate | KENESTER HMS | Humko Chemical |
| Menthyl anthranilate | SUNAROME UVA | Felton Worldwide |
| Octocrylene | UVINUL N-539 | BASF Chemical Co. |
| Octyl dimethyl PABA | AMERSCOL | Amerchol Corp. |
| Octyl methoxycinnamate | PARSOL MCX | Bernel Chemical |
| Octyl salicylate | SUNAROME WMO | Felton Worldwide |
| PABA | PABA | National Starch |
| 2-Phenylbenzimidazole-5-sulphonic acid | EUSOLEX 6300 | EM Industries |
| TEA salicylate | SYBARINE W | Felton Worldwide |
| 2-(4-Methylbenztilene)-camphor | EUSOLEX 6300 | EM Industries |
| Benzophenone-1 | UVINUL 400 | BASF Chemical Co. |
| Benzophenone-2 | UVINUL D-50 | BASF Chemical Co. |
| Benzophenone-6 | UVINUL D-49 | BASF Chemical Co. |
| Benzophenone-12 | UVINUL 408 | BASF Chemical Co. |
| 4-Isopropyl dibenzoyl methane | EUSOLEX 8020 | EM Industries |
| Butyl Methoxy dibenzoyl methane | PARSOL 1789 | Givaudan Corp. |
| Etocrylene | UVINUL N-35 | BASF Chemical Co. |

Inorganic sunscreen actives may also be employed such as microfine titanium dioxide, zinc oxide, polyethylene, polyamides (e.g. nylon) and various other polymers. Amounts of the sunscreen agents (whether organic or inorganic) will generally range from 0.1 to 30%, preferably from 2 to 20%, optimally from 4 to 10% by weight.

Compositions of the present invention will utilize a pharmaceutically acceptacle carrier. The carrier may either be aqueous, anhydrous or an emulsion. Preferably the compositions are aqueous, especially water and oil emulsions of the W/O or O/W variety. Water when present will be in amounts which may range from 5 to 95%, preferably from 20 to 70%, optimally between 35 and 60% by weight.

Besides water, relatively volatile solvents may also serve as carriers within compositions of the present invention. Most preferred are monohydric $C_1$–$C_3$ alkanols. These include ethyl alcohol, methyl alcohol and isopropyl alcohol. The amount of monohydric alkanol may range from 1 to 70%, preferably from 10 to 50%, optimally between 15 to 40% by weight.

Emollient materials may also serve as pharmaceutically acceptable carriers. These may be in the form of silicone oils and synthetic esters. Amounts of the emollients may range anywhere from 0.1 to 30%, preferably between 1 and 20% by weight.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms.

Linear volatile silicone materials generally have viscosities less than about 5 centistokes at 25° C. while cyclic materials typically have viscosities of less than about 10 centistokes.

Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C.

Among the ester emollients are:

(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.

(2) Ether-esters such as fatty acid esters of ethoxylated fatty alcohols.

(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate and arachidyl behenate.

(5) Sterols esters, of which cholesterol fatty acid esters are examples thereof.

Fatty acids having from 10 to 30 carbon atoms may also be included as pharmaceutically acceptable carriers for compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol-type may also be employed as pharmaceutically acceptable carriers in compositions of this invention. The humectant aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol. The amount of humectant may range anywhere from 0.5 to 30%, preferably between 1 and 15% by weight of the composition.

Thickeners may also be utilized as part of the pharmaceutically acceptable carrier of compositions according to the present invention. Typical thickeners include crosslinked acrylates (e.g. Carbopol 982®), hydrophobically-modified acrylates (e.g. Carbopol 1382®), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Amounts of the thickener may range from 0.0001 to 5%, usually from 0.001 to 1%, optimally from 0.01 to 0.5% by weight.

Collectively the water, solvents, silicones, esters, fatty acids, humectants and/or thickeners will constitute the pharmaceutically acceptable carrier in amounts from 1 to 99.9%, preferably from 80 to 99% by weight.

Cosmetic compositions of the present invention may be in any form. These forms may include emulsified systems such as lotions and creams, microemulsions, roll-on formulations, mousses, ointments (hydrophilic and hydrophobic), aerosol and non-aerosol sprays and pad-applied formulations.

Surfactants may also be present in compositions of the present invention. Total concentration of the surfactant will range from 0.1 to 40%, preferably from 1 to 20%, optimally from 1 to 5% by weight of the composition. The surfactant may be selected from the group consisting of anionic, nonionic, cationic and amphoteric actives. Particularly preferred nonionic surfactants are those with a $C_{10}$–$C_{20}$ fatty alcohol or acid hydrophobe condensed with from 2 to 100 moles of ethylene oxide or propylene oxide per mole of hydrophobe; $C_2$–$C_{10}$ alkyl phenols condensed with from 2 to 20 moles of alkylene oxide; mono- and di- fatty acid esters of ethylene glycol; fatty acid monoglyceride; sorbitan, mono- and di- $C_8$–$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$–$C_{20}$ acyl isethionates, acyl glutamates, $C_8$–$C_{20}$ alkyl ether phosphates and combinations thereof.

Preservatives can desirably be incorporated into the compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2% by weight of the composition.

Keratolytic agents such as $C_2$–$C_{25}$ (α-hydroxy carboxylic and β-hydroxycarboxylic acids may also be incorporated into compositions of this invention. Illustrative materials are glycolic, lactic, salicylic, α-hydroxyoctanoic acids and salts thereof. The salts may be selected from alkalimetal, ammonium and $C_1$–$C_{20}$ alkyl or alkanolammonium counterions. Levels of these keratolytic agents may range from 0.001 to 10%, preferably between 0.2 and 8%, optimally between 1 and 4% by weight.

Minor adjunct ingredients may also be present in the compositions. Among these may be the water-insoluble vitamins such as Vitamin A Palmitate, Vitamin E Acetate and DL-panthenol.

Colorants, fragrances, opacifiers and abrasives may also be included in compositions of the present invention. Each of these substances may range from about 0.05 to about 5%, preferably between 0.1 and 3% by weight.

The following Examples will more fully illustrate embodiments of this invention. All parts, percentages and proportions referred to herein and in the appended claims are by weight unless otherwise indicated.

EXAMPLE 1

A clinical test was performed to evaluate the efficacy of vanillin in lightening skin. More specifically, the evaluation focused upon reduction of color intensity of hyperpigmented lesions.

Ten women panelists were involved in the clinical study. These panelists were pre-screened from a group of 120 women. Ages were between 45 and 65 years old. The forearms and hands of the selected panelists were required to exhibit a light to moderate level of sun damage, i.e. hyperpigmentation, freckling, mottled appearance, wrinkling and uneven color. Each panelist received two products for twice daily (morning and evening) application after washing. One product was applied to the left lower arm and hand. The second product was applied to the right lower arm and hand. Each panelist demarcated treated from untreated skin by measuring down from the elbow joint using four fingers of the hand held flat at the joint. No product was applied above the lowest finger. Skin color for each panelist was then assessed at baseline and every two weeks over the six week treatment course. Each panelist was required to avoid exposing arms and hands to sunlight over the course of the study. Incidental exposure (i.e. 5–10 minutes) was however acceptable. When any panelist thought that her hands and arms would be exposed to sunlight for extended periods, she was encouraged to wear a long sleeve garment and use a sunscreen with SPF of at least 15.

A Scopeman Fiber Optic microscope was used to capture still analog video images of specific hyperpigmented lesions on the dorsal surface of the hands and forearms of each panelist. The images were processed into a CP Vision Logic, Digital Image Processor. Utilizing this equipment it was possible to measure variants of the hyperpigmented lesions and the surrounding "normal" skin, densitometric reading of each spot, and a size determination of each lesion. The base composition utilized as a control had the formulation as listed in Table II.

TABLE II

| BASE COMPOSITION | |
|---|---|
| INGREDIENT | WEIGHT % |
| Lactic Acid | 8.0 |
| Butylene Glycol | 3.0 |

TABLE II-continued

BASE COMPOSITION

| INGREDIENT | WEIGHT % |
|---|---|
| Stearic Acid | 3.0 |
| Potassium Hydroxide | 2.7 |
| Isostearyl Palmitate | 2.0 |
| Glycerin | 2.0 |
| PEG-100 Stearate | 2.0 |
| Glyceryl Hydroxystearate Acid | 1.5 |
| Stearyl Alcohol | 1.5 |
| Triethanolamine | 1.2 |
| $C_{12-15}$ Alkyl Octanoate | 1.0 |
| Dimethicone | 1.0 |
| Sorbitan Stearate | 1.0 |
| Methylparaben | 0.15 |
| Magnesium Aluminum Silicate | 0.6 |
| Cholesterol | 0.5 |
| Hydroxyethylcellulose | 0.5 |
| Xanthan Gum | 0.2 |
| Propylparaben | 0.1 |
| Disodium EDTA | 0.05 |
| BHT | 0.05 |
| Simethicone | 0.01 |
| Water | balance to 100 |

Color intensity diminished in the skin of nine of the ten panelists when 2% vanillin was included in the base composition. Overall, there was a 19% color intensity reduction of hyperpigmented lesions over a six week period. Reduction of color with the base composition is believed to result from the presence of lactic acid. Addition of vanillin still further reduced the color intensity of hyperpigmented lesions by 37.6% over the six week period. Statistically, "p" was less than 0.002. Table III outlines individual panelist responses.

TABLE III

COLOR INTENSITY REDUCTION

| PANELIST NO. | BASE (CONTROL) | 2% VANILLIN IN BASE |
|---|---|---|
| 1 | 7.8 | 33.5 |
| 2 | 12.1 | 48.2 |
| 3 | 30.2 | 33.5 |
| 4 | 2.8 | 47.6 |
| 5 | 17.1 | 35.3 |
| 6 | 11.3 | 38.1 |
| 7 | 0.0 | 22.3 |
| 8 | 34.6 | 36.9 |
| 9 | 37.3 | 26.0 |
| 10 | 37.4 | 54.9 |

EXAMPLE 2

A microemulsion formulation according to the present invention is outlined under Table IV.

TABLE IV

| INGREDIENT | WEIGHT (%) |
|---|---|
| PPG-5-Ceteth-20 | 4.00 |
| PEG-40 Hydrogenated Castor Oil | 1.75 |
| Polyglyceryl-10 Decaoleate | 10.50 |
| PEG-8 Caprylic/capric Glycerides | 10.50 |
| SD Alcohol 40 | 12.00 |
| Isodecyl Neopentanoate | 16.00 |
| Glyceryl Trioctanoate | 8.00 |
| DC Silicone Fluid 344 ® | 8.50 |
| Propylparaben | 0.15 |

TABLE IV-continued

| INGREDIENT | WEIGHT (%) |
|---|---|
| Isostearic Acid | 2.50 |
| Vanillin | 3.75 |
| Hydroxycaprilic Acid | 0.10 |
| Tocopheryl Acetate | 0.25 |
| Phenoxyethanol | 0.30 |
| Deionized Water | Q.S |

EXAMPLE 3

A skin lotion (water in oil type) formulation according to the present invention is outlined under Table V.

TABLE V

| INGREDIENT | WEIGHT (%) |
|---|---|
| Cetyl Dimethicone | 2.50 |
| DC Silicone Fluid 344 ® | 4.00 |
| DC Silicone Fluid 200 ® (20 CST) | 1.25 |
| Squalane | 1.75 |
| Octyl Octanoate | 2.00 |
| Zinc Myristate | 1.25 |
| Dimethicone Copolyol | 2.50 |
| Butylene Glycol | 4.50 |
| Glycerin | 1.50 |
| Sodium Hyaluronate | 1.00 |
| Vanillic Acid | 6.00 |
| Salacos HS ® | 2.50 |
| Isostearic Acid | 2.50 |
| Isononyl Isononanoate | 3.75 |
| Hydroxycaprilic Acid | 0.10 |
| Methylparaben | 0.20 |
| Propylparaben | 0.10 |
| Tocopheryl Acetate | 0.55 |
| Phenoxyethanol | 0.20 |
| Deionized Water | Q.S |

EXAMPLE 4

A skin cream (oil in water type) with sunscreen formulation according to the present invention is outlined under Table VI.

TABLE VI

| INGREDIENT | WEIGHT (%) |
|---|---|
| Hydroxyethylcellulose | 0.50 |
| Magnesium Aluminum Silicate | 0.75 |
| Cocoa Butter | 1.25 |
| Squalene | 1.05 |
| Isostearyl Isononanoate | 2.25 |
| DC Silicone Fluid 200 ® (50 CST) | 1.25 |
| DC Silicone Fluid 200 ® (100 CST) | 0.50 |
| Butylene Glycol | 3.00 |
| Parsol MCX ® | 3.00 |
| Parsol 1789 ® | 3.00 |
| Glycerin | 2.50 |
| Sodium Hyaluronate | 0.50 |
| Vanillin | 5.00 |
| Glycereth-7 Hydroxystearate | 1.50 |
| Stearic Acid | 3.50 |
| Cetyl/Stearyl Alcohol | 2.55 |
| Sodium PCA | 2.10 |
| Glyceryl Hydroxystearate | 1.25 |
| Tocopherol | 0.35 |
| Methylparaben | 0.20 |
| Propylparaben | 0.10 |
| Glydant ® | 0.30 |
| Steareth-20 | 1.20 |
| Disodium EDTA | 0.05 |

TABLE VI-continued

| INGREDIENT | WEIGHT (%) |
| --- | --- |
| Triethanolamine | 1.50 |
| Deionized Water | Q.S |

EXAMPLE 5

An anhydrous serum with inorganic (titanium dioxide) sunscreen formulation according to the present invention is outlined under Table VII.

TABLE VII

| INGREDIENT | WEIGHT (%) |
| --- | --- |
| Zinc Oxide | 8.00 |
| Sepigel 305 ® | 1.50 |
| SD Alcohol 40 (200°) | 20.00 |
| Squalene | 1.05 |
| Octyl Isononanoate | 2.25 |
| DC Silicone Fluid 200 ® (10 CST) | 5.25 |
| Isononyl Isononanoate | 30.00 |
| Butylene Glycol | 1.00 |
| Tocopheryl Linoleate | 0.50 |
| Propylparaben | 0.10 |
| Iocopheryl Acetate | 0.10 |
| Vanillin | 2.75 |
| Dimethiconol | 2.50 |
| DC Silicone Fluid 344 ® | QS |

EXAMPLE 6

A skin lotion (oil in water type) formulation according to the present invention is outlined under Table VIII.

TABLE VIII

| INGREDIENT | WEIGHT (%) |
| --- | --- |
| Xanthan Gum | 0.20 |
| Magnesium Aluminum Silicate | 0.75 |
| Shea Butter Glycerides | 1.25 |
| Squalene | 2.25 |
| Coco Caprylate/Caprate | 3.25 |
| DC Silicone Fluid 200 ® (50 CST) | 0.75 |
| DC Silicone Fluid 200 ® (50 CST) | 0.50 |
| Butylene Glycol | 3.00 |
| Glycerin | 2.00 |
| Sodium Hyaluronate | 0.35 |
| Vanillic Acid | 3.50 |
| Cetyl Alcohol | 1.00 |
| DEA-Cetyl Phosphate | 2.15 |
| Saccharide Isomerate | 1.00 |
| Sodium PCA | 2.10 |
| Sucrose Laurate | 0.50 |
| Ceteth-2 | 0.50 |
| Methylparaben | 0.20 |
| Propylparaben | 0.10 |
| Germall II ® | 0.30 |
| Steareth-20 | 1.20 |
| Tocopheryl Acetate | 0.20 |
| Disodium EDTA | 0.05 |
| Lactic Acid | 0.10 |
| Deionized Water | Q.S |

EXAMPLE 7

A protective skin lotion with sunscreen formulation according to the present invention is outlined under Table IX.

TABLE IX

| INGREDIENT | WEIGHT (%) |
| --- | --- |
| Xanthan Gum | 0.15 |
| Sepigel 501 ® | 1.50 |
| Shea Butter | 1.50 |
| Squalene | 2.00 |
| Coco Caprylate/Caprate | 2.25 |
| Propylene Glycol Dicaprylate/Dicaprate | 3.55 |
| DC Silicone Fluid 200 ® (20 CST) | 0.50 |
| DC Silicone Fluid 200 ® (350 CST) | 1.00 |
| Butylene Glycol | 3.00 |
| Glycerin | 1.00 |
| Sodium Hyaluronate | 0.35 |
| Vanillin | 3.00 |
| Cetyl Alcohol | 1.00 |
| DEA-Cetyl Phosphate | 1.25 |
| Parsol MCX ® | 6.00 |
| Benzophenone-3 | 3.00 |
| Ceteth-2 | 0.50 |
| Ceteareth-20 | 1.20 |
| Methylparaben | 0.30 |
| Propyplaraben | 0.15 |
| Glydant ® | 0.20 |
| Aloe Vera Gel | 2.00 |
| Tocopheryl Acetate | 0.30 |
| Disodium EDTA | 0.05 |
| Deionized Water | Q.S |

The foregoing description and Examples illustrate selected embodiments of the present invention. In light thereof, various modifications will be suggested to one skilled in the art, all of which are within the spirit and purview of this invention.

What is claimed is:

1. A method for lightening the color of skin comprising applying to the skin a compound of the structure (I):

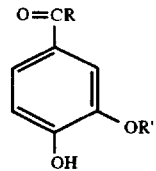

(I)

wherein R is selected from the group consisting of hydrogen, hydroxy and $C_1$–$C_{30}$ alkyl or aryl groups radicals; and $R^1$ is selected from the group consisting of hydrogen and $C_1$–$C_{30}$ alkyl or aryl radicals.

2. The method according to claim 1 wherein the active is selected from the group consisting of vanillin and vanillic acid.

3. The method according to claim 1 wherein skin lightening removes agespots and freckles.

4. The method according to claim 1 wherein skin lightening eliminates hyperpigmentation.

5. The method according to claim 1 further comprising a sunscreen present in an effective amount to shield skin from ultra-violet radiation in the range from 290 to 400 nm.

6. The method according to claim 1 further comprising applying to the skin a $C_2$–$C_{30}$ α-hydroxycarboxylic acid or β-hydroxycarboxylic acid and salts thereof.

7. A skin lightening cosmetic composition comprising:
    (i) an effective amount to achieve skin lightening of an active having structure (I):

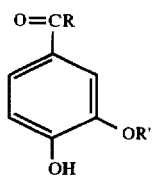

(I)

wherein R is selected from the group consisting of hydrogen, hydroxy and $C_1$–$C_{30}$ alkyl or aryl groups radicals; and $R^1$ is selected from the group consisting of hydrogen and $C_1$–$C_{30}$ alkyl or aryl radicals;

(ii) from 0.1 to 30% by weight of a sunscreen agent; and (iii) a pharmaceutically acceptable carrier to deliver structure (I) and the sunscreen agent.

8. The composition according to claim 7 wherein the active is selected from the group consisting of vanillin and vanillic acid.

9. The composition according to claim 7 wherein skin lightening removes agespots and freckles.

10. The composition according to claim 7 wherein skin lightening eliminates hyperpigmentation.

11. The composition according to claim 7 further comprising a sunscreen agent present in an effective amount to shield skin from ultra-violet radiation in the range from 290 to 400 nm.

12. The composition according to claim 7 further comprising from 0.001 to 10% of a $C_2$–$C_{30}$ α-hydroxycarboxylic acid or β-hydroxycarboxylic acid and salts thereof.

* * * * *